United States Patent

Kaestle et al.

[11] Patent Number: 6,122,535
[45] Date of Patent: Sep. 19, 2000

[54] METHOD AND APPARATUS FOR DETERMINING THE CONCENTRATION OF A COMPONENT

[75] Inventors: Siegfried Kaestle, Nufringen; Hedwig Block; Michael Block, both of Boeblingen, all of Germany

[73] Assignee: Hewlett-Packard Company, Palo Alto, Calif.

[21] Appl. No.: 09/037,947

[22] Filed: Mar. 10, 1998

[30] Foreign Application Priority Data

Apr. 12, 1997 [EP] European Pat. Off. .............. 97106051

[51] Int. Cl.[7] ...................................................... A61B 5/00
[52] U.S. Cl. ............................................. 600/322; 600/336
[58] Field of Search ................................... 600/310, 322, 600/323, 336, 473, 476

[56] References Cited

U.S. PATENT DOCUMENTS 5,553,614 9/1996 Chance ..................................... 600/407

FOREIGN PATENT DOCUMENTS

0335357A2 3/1989 European Pat. Off. .
WO 96/12435 10/1995 WIPO .

OTHER PUBLICATIONS

Comput. Biol. Med., vol. 26, No. 2, pp. 143–159, XP 002039742, T. L. Rusch et al, "Signal Processing Methods for Pulse Oximetry", 1996.

Primary Examiner—Eric F. Winakur

[57] ABSTRACT

A method of determining at least the concentration of a component from the intensity of electromagnetic waves with at least two selected wavelengths which are reflected by human tissue or transmitted through human tissue comprises firstly the step of converting the intensities of the received electromagnetic signals into at least one first and one second time-dependent electric signal. Then a time-discrete transformation of the first and of the second electric signal into the frequency domain is performed to determine first and second spectral values of the first and of the second signal. Complex combinatorial values are formed from said first and second spectral values and physiologically relevant combinatorial values are selected by evaluating the complex combinatorial values according to given criteria for the physiological relevance thereof. Finally, the concentration of the component is calculated by using the selected combinatorial values or by using the frequencywise-associated spectral values.

14 Claims, 4 Drawing Sheets

METHOD AND APPARATUS FOR DETERMINING THE CONCENTRATION OF A COMPONENT

FIELD OF THE INVENTION

The present invention refers to a method and an apparatus for determining the concentration of a component from the intensity of electromagnetic waves with at least two selected wavelengths which are reflected by human tissue or transmitted through human tissue, e.g. for determining a gas saturation, particularly the oxygen saturation.

The methods and apparatus according to the present invention can, for example, be used in an advantageous manner for measuring and calculating the oxygen saturation.

BACKGROUND OF THE INVENTION

Oxygen saturation is a clinically very relevant parameter to assess the condition of a patient. Particularly in the operating room, the oxygen saturation of the blood gives an indication of the patient's condition, its supply with oxygen and other physiological factors.

One possibility to obtain a very precise value of the patient's oxygen saturation is to take a blood sample and analyze it in a blood gas analyzer. Despite the high precision of this method, it is an invasive technique and this means that it cannot performed frequently, i.e. does not allow continuous monitoring. Therefore, significant changes in the oxygen saturation value may be missed. Last not least, it is understood that an invasive technique is not the preferred way to monitor a patient.

It is therefore highly desirable to measure oxygen saturation non-invasively. This can be achieved by a technique called oximetry.

An oximeter usually comprises two or more light sources of different wave length. The light is irradiated on human flesh, and either the intensity of the light transmitted through the flesh, or the intensity of the reflected light is measured. In more general terms, "light" does not only mean electromagnetic waves in the visible spectrum. For example, the most common oximeters use one wavelength in the visible spectrum and another wavelength in the infrared spectrum. Such a oximeter is described for example in "A New Family of Sensors for Pulse Oximetry", S. Kästle, F. Noller et al, February 1997, Hewlett-Packard Journal. For more details of the theory of oxygen saturation measurement, reference is made to former publications on this subject. e.g. U.S. Pat. No. 4,167,331 or EP-A-262778 (the latter patent application contains a quite complete breakdown of the theory).

For obtaining a saturation value, a set of a value quadruple is always necessary which consists of a pair of values for each of the two wavelengths. e.g. red and infrared. ($R_1$, $IR_1$) and ($R_2$, $IR_2$). Normally, a first pair of values is used as raw curve samples at time 1 and a second pair of values as raw curve samples at time 2. The assumption underlying this course of action is that the samples differ at time 1 and time 2 only with regard to a change in level caused by a change in the arterial blood volume. Normally, the diastolic Pleth value (maximum) is used as the first pair of values and the systolic Pleth value (minimum) is used as the second sample.

Speaking more generally, arbitrary, e.g. composite and/or averaged values for red R and infrared IR can be used, provided that the pairs R and IR belong together signalwise, and provided that the data underlying the pairs of values 1 and 2 only differ with regard to a change in the arterial blood.

A ratio of the two pairs of values can then be calculated as follows:

$$\text{ratio} = ln(R_1/R_2)/ln(IR_1/IR_2) \quad (1)$$

The oxygen saturation can then be calculated on the basis of this ratio in the manner known.

$$SpO2 = f(\text{ratio}) \quad (2)$$

In the method described hereinbefore, the raw signals obtained on the basis of the intensity of electromagnetic waves or the composite or averaged values obtained from said raw signals are considered in the time domain for determining the oxygen saturation. However, if a disturbance signal exists, it is impossible to separate the useful signal and the disturbance signal in the time domain if they are constantly present. The least-square-x/y method in the time domain is normally always falsified and, if the disturbances are strong disturbances in the order of S/N=1, it is no longer of any use.

SUMMARY OF THE INVENTION

Starting from the above-mentioned prior art, it is the object of the present invention to provide a methods and apparatus which are used for determining at least the concentration of a component from the intensity of electromagnetic waves with at least two selected wavelengths reflected e.g. by human tissue or transmitted through human tissue and which permit a reliable determination of the concentration of the component even if strong disturbances exist.

In accordance with a first aspect, the present invention provides a method of determining at least the concentration of a component from the intensity of electromagnetic waves with at least two selected wavelengths which are reflected by human tissue or transmitted through human tissue, said method comprising the following steps:

converting the intensities of the received electromagnetic signals into at least one first and one second time-dependent electric signal;

time-discretely transforming the first and of the second electric signal into the frequency domain for determining first and second spectral values of the first and of the second signal;

forming complex combinatorial values from said first and second spectral values;

selecting physiologically relevant combinatorial values by evaluating the complex combinatorial values according to given criteria for the physiological relevance thereof; and calculating the concentration of the component making use of the selected combinatorial values or making use of frequencywise-associated spectral values.

According to a preferred embodiment of the present invention, for determining the concentration of a component an electromagnetic wave in the red region and an electromagnetic wave in the infrared region are used as the at least two selected wavelengths. The time-dependent signals received at these wavelengths are preferably subjected to preprocessing for removing time-dependent drifts from said first and second signals prior to carrying out the time-discrete transformation into the frequency domain. The subsequent time-discrete transformation is preferably carried out by means of a Fourier transformation making use of a suitable time window. In accordance with a preferred embodiment, the selection of the physiologically relevant combinatorial values is carried out on the basis of maximum value ranges in the amount spectrum of the complex combinatorial values. In accordance with preferred embodiments of the present invention, also a pulse rate and a perfusion index are determined on the basis of the selected combinatorial values or by making use of frequencywise-associated spectral values.

At least two of the criteria following hereinbelow are used as given criteria for the physiological relevance of the complex combinatorial values: width of the maximum value range; frequency of the maximum value in the maximum value range; gravity frequency of all combinatorial values in the maximum value range; position of the maximum value range with regard to farther maximum value ranges in the amount spectrum; saturation value obtained for the maximum value in the maximum value range; the perfusion index determined from said maximum value in said maximum value range; the pulse rate determined from the gravity frequency in said maximum value range.

The steps of the method according to the present invention are normally cyclically repeated; the saturation values obtained in the course of several cycles can be subjected to filtering and/or averaging. The given criteria used can additionally be the following ones: deviation of the frequency of the maximum value of the maximum value range and/or of the perfusion index and/or of the saturation value from reference values determined in the course of a preceding cycle.

In contrast to known pulse oximetry methods comprising the steps of filtering signals in the time domain, evaluating them and relating then the signals that have been obtained for red and infrared, the fundamental idea of the present invention is based on the concept of subjecting the signals to a frequency transformation, whereupon the transformed signals are "filtered", evaluated and related so as to form a ratio. When considered in the frequency domain, the fundamental wave and all the harmonic waves of the arterial pulse provide individually and together a correct ratio. All the other frequency components, whether noise or motion disturbances, normally differ from the "comb spectrum" of a blood pulse. At least, the disturbers cannot be found in identical proportions on each frequency component.

When used for determining the concentration of a component, e.g. the gas saturation, from the intensity of electromagnetic waves with at least two selected wavelengths which are reflected by human tissue or transmitted through human tissue, the method according to the present invention provides reliable results when perfusion is high and when perfusion is low. Especially in the case of signals with low perfusion and motion disturbances, so-called motion artifacts, caused by motions of the object to be analyzed, precise results are obtained in a very reliable manner.

In accordance with a second aspect, the present invention provides a method of determining at least the concentration of a component, e.g. a gas saturation, from the intensity of electromagnetic waves with at least two selected wavelengths which are reflected by human tissue or transmitted through human tissue, said method comprising the following steps:

converting the intensities of the received electromagnetic signals into at least one first and one second time-dependent electric signal;

time-discretely transforming the first and of the second electric signal into the frequency domain for determining first and second spectral values of the first and of the second signal; selecting physiologically relevant first and second spectral values by evaluating said first and second spectral values according to given criteria for the physiological relevance thereof; and calculating the concentration of the component making use of the selected first and second spectral values.

The present invention additionally provides apparatus for carrying out the methods described hereinbefore.

BRIEF DESCRIPTION OF THE DRAWINGS

In the following, preferred embodiments of the present invention are explained in detail making reference to the drawings enclosed, in which.

DETAILED DESCRIPTION OF THE PREFERRED EMBODIMENT

Figure 1:
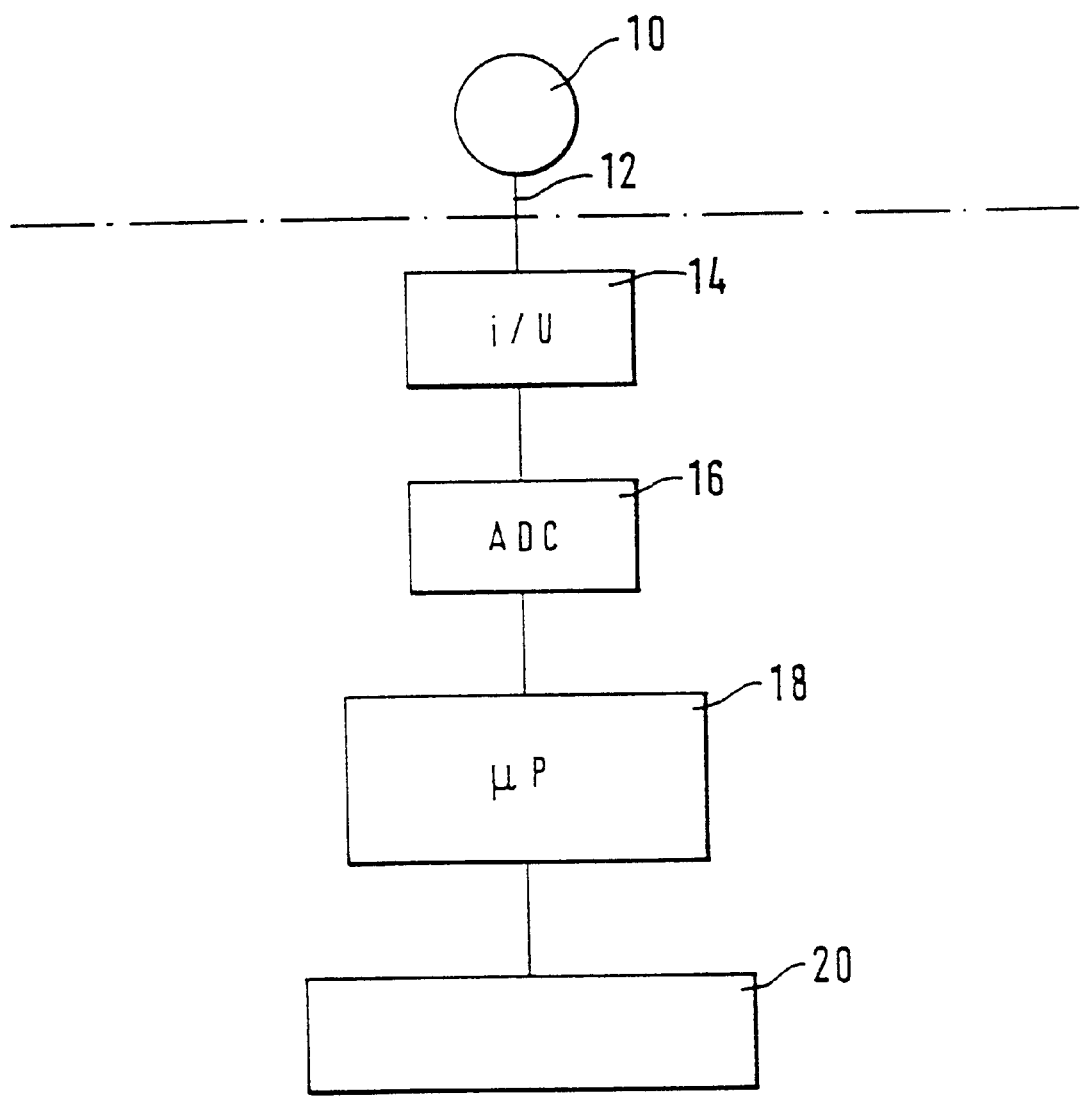
FIG. 1 shows a schematic block diagram representing an oximeter.

FIG. 1 shows the basic structure of an oximeter which is adapted to be used for carrying out the method according to the present invention. The oximeter includes a sensor device 10 for transmitting and receiving electromagnetic waves with at least two selected wavelengths. In accordance with a preferred embodiment of the present invention, one wavelength in the visible red spectrum and another wavelength in the infrared spectrum are used for this purpose. The signal produced by the photoelectric receiver in the sensor device 10 is fed through a line 12 into a current-to-voltage converter unit 14 and, subsequently, into an analog-to-digital converter 16 producing a digital representation of the intensity measured. This digital value is then fed into a microprocessor 18 working under the control of a program memory 20. The program memory 20 contains the whole code which is necessary for the processor for determining the oxygen saturation and, if desired, also a perfusion index or a pulse rate, as will be explained in detail hereinbelow. The program code in said memory 20 instructs the processor 18 to carry out all the steps which are necessary for the method according to the present invention.

It is obvious that, instead of the special arrangement described hereinbefore, it is possible to use arbitrary processing units which are known in the field of technology and which are capable of carrying out the methods according to the present invention. Such processing units can, for example, comprise displays and input devices and additional memory and accessory arrays in the manner known.

Figure 2:
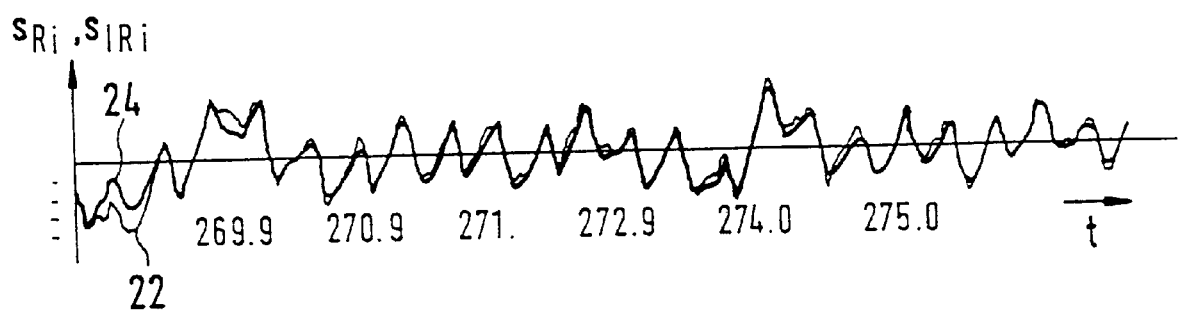
FIG. 2 shows a representation of preprocessed raw signals I and IR in the time domain.

According to preferred embodiments of the present invention, the electric raw signals, which have been obtained on the basis of the intensity of electromagnetic waves at at least two selected wavelengths, typically red and infrared, are first subjected to preprocessing so as to remove time-dependent drifts from said first and second signals. In FIG. 2, raw curves R (red) and IR (infrared), which have been subjected to such preprocessing, are shown.

In the following, a brief explanation of this preprocessing will be given. The preprocessing aims at separating, if possible, all the time-dependent superpositions from the raw signals. For this purpose, a continuous average value is formed on the basis of the raw waves $R_i$ and $IR_i$ for determining a so called baseline according to the following equations:

$$M_{Ri} = 1/T \sum_{i-T/2}^{i+T/2} R_i \quad (3a)$$

$$M_{IRi} = 1/T \sum_{i-T/2}^{i+T/2} IR_i \quad (3b)$$

wherein
i=the continuous sample;
$M_{Ri}$, $M_{IRi}$=the continuous average values of $R_i$ and $IR_i$ symmetrically around said sample i;
T=period of averaging (e.g. one second).

The baseline is now eliminated from the raw signals by means of the following equations:

$$S_{Ri} = ln(R_i/M_{Ri}) \quad (4a)$$

$$S_{IRi} = ln(IR_i/M_{IRi}) \quad (4b)$$

$S_{Ri}$ and $S_{IRi}$ now represent the continuous samples of the original raw signals for red and infrared in the time domain.

Examples of such time-dependent samples $S_{Ri}$, curve 22, and $S_{IRi}$, curve 24, are shown in the form of curves in FIG. 2. The ordinate represents the time in the diagram according to FIG. 2, whereas the abscissa represents normalized amplitudes of $S_{Ri}$ and $S_{IRi}$. In view of the fact that the raw curves were sampled at 125 Hz in the above example, but are strongly band-limited to 10 Hz, redundancy was additionally eliminated in the course of the preprocessing and sampled down by the factor of 4 to 31,25 Hz.

The above-described preprocessing of the raw signal provides a plurality of advantages. On the one hand, the signals are normalized, whereby the range of values becomes smaller and this is advantageous with regard to integer processing. Furthermore, the signal ratio of each sample pair R to IR already provides a ratio that can be utilized according to equation (2). Furthermore, linear drifts of the signals are completely eliminated by the symmetric averaging.

According to the present invention, the signals present in the time domain are now subjected to a time-discrete transformation into the frequency domain. According to the preferred embodiment, the preprocessed samples $S_{Ri}$ and $S_{IRi}$ are subjected to a fast Fourier transformation (FFT) making use of suitable windowing. The selection of the windowshape is uncritical in this connection. In the embodiment described, the known cos-shaped Hanning window has been used, which combines advantageous properties with regard to a minimum peak enlargement and small secondary peaks. What is more important is the window length. In this connection, a compromise must be made between a window length that is sufficiently long for realizing a good frequency resolution, i.e. many points, and a window length that is sufficiently short for rapid changes of the signal frequencies, of the pulse rate and of intermittent disturbances. In the preferred embodiment, a window of 8 seconds, n=256 samples, was used. Making use of such a window, a sufficient frequency resolution of 1/(32 ms·n)=0.12 Hz is realized. Hence, 82 values are obtained in the frequency band of interest from 0 to 10 Hz.

Figure 3:
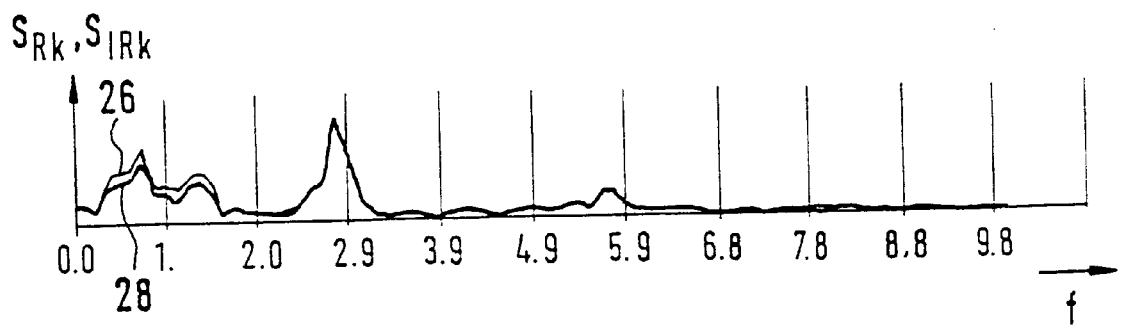
FIG. 3 shows a representation of the Fourier transformed values of the signals shown in FIG. 2.

The Fourier transformed values $S_{Rk}$, curve 26, and $S_{IRk}$, curve 28, of the signals of FIG. 2 are shown in FIG. 3, said Fourier transformed values being determined in the way described hereinbefore. The ordinate of the diagram of FIG. 3 represents the frequency, whereas the abscissa again represents normalized amplitudes of $S_{Rk}$ and $S_{IRk}$. Due to the baseline preprocessing described hereinbefore, the DC component is practically equal to zero with the exception of rounding errors.

When $\hat{S}$ is defined as amplitude spectrum (absolut value of the Fourier transformed values) of the time function s (equations 4a and 4b), a ratio can be formed on the basis of the ratio of the coefficients for each pair of frequency points:

$$Ratio_k = \hat{S}_{Rk}/\hat{S}_{IRk} \quad (5)$$

wherein k stands for the respective frequency base points.

For the peak of the spectrum, which originate from a blood pulse, a ratio should be obtained in this way which leads to the true Sp02 value (i.e. oxygen saturation value). For spectral components lying outside of the regions around the fundamental and harmonic waves of the blood pulse, ratio results are obtained which must be regarded as disturbers and which must be eliminated. This elimination will be explained in detail hereinbelow.

In a continuous mode of operation, the FFT window is advanced by a predetermined period of time, e.g. 1 second, in each case. Hence, a new spectrum (pair) is determined for each predetermined period of time. Although this results in a ⅞ window overlap and, consequently, in great redundancy, it turned out that the spectral changes occurring in the course of ⅛ displacement already justify a new calculation cycle. The method according to the present invention is therefore preferably run through cyclically, the duration of one cycle being e.g. 1 second.

When, in the case of an alternative embodiment of the method according to the present invention, the above-described preprocessing of the time-dependent signals is dispensed with, the baseline or the reference value can be determined in the frequency domain in some other manner, e.g. as the DC component of the signal in the FFT window or as output signal of a normal causal lowpass filter having a sufficiently low limiting frequency (e.g. in the region of 0.5 Hz). In this case, the fast Fourier transformation, is carried out directly on the raw signals obtained.

Figure 4:
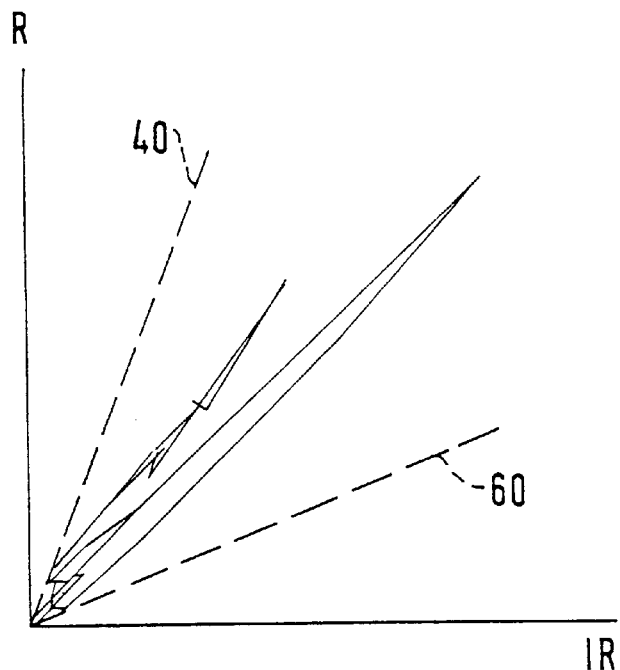
FIG. 4 shows a complex representation of the signals shown in FIG. 3.

In the preferred embodiment of the method according to the present invention, complex combinatorial values are now formed on the basis of the Fourier transformed values. In order to make this more easily comprehensible, it can be considered as a parametric x-y representation of the Fourier transformed values. When the infrared spectrum is plotted in the x-direction and the red spectrum in the y-direction, a representation is obtained which has needlelike tips. Such a representation for the spectra shown in FIG. 3 is shown in FIG. 4. These "needles" correspond to the peaks of the spectra. For undisturbed signals very slim needles are obtained, the respective needles for the fundamental and harmonic waves lying one on top of the other. The direction of the needles corresponds to the saturation. This means, in concrete terms, that the mean gradient of a needle is the ratio searched for.

Various disturbance frequency components lie outside of the needle generated by a blood pulse. Background noise and minor disturbances cause an accumulation of points around the origin in the x-y representation, which could be referred to as "cloud". Furthermore, said background noise and said minor disturbances cause an offset of the needles.

Also correlated disturbances of the red spectrum and of the infrared spectrum, such as motion artifacts, which have similar spectral components can be discerned as extra needles and are normally not in the regression with the useful-signal needles of the blood pulse spectrum. The broken line 40 in FIG. 4 indicates an SpO2 limit of 0 percent, whereas the broken line 60 indicates an SpO2 limit of 100 percent.

For algorithmically identifying the "needles", it is first of all necessary to determine the length of said needles. For this purpose, a so-called distance spectrum is calculated on the basis of the amplitudes $\hat{S}_{Rk}$ and $\hat{S}_{IRk}$ of the red spectrum and of the infrared spectrum, the values of said distance spectrum being determined according to the following equation at each frequency k:

$$A_k = \sqrt{\hat{S}_{Rk}^2 + \hat{S}_{IRk}^2} \tag{6}$$

Figure 5:
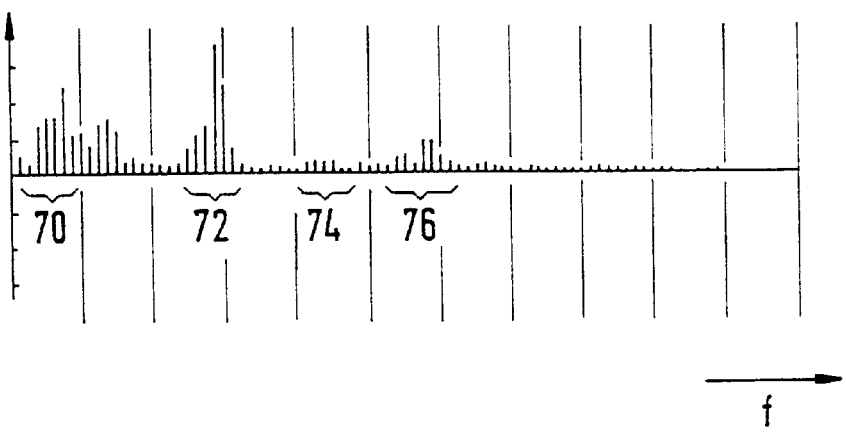
FIG. 5 shows a representation of the amount spectrum of complex combinatorial values determined on the basis of the signals shown in FIG. 3.

These values $A_k$ therefore represent the amount of the complex combinatorial values determined on the basis of the red and infrared spectra. The phase of the complex combinatorial values is given by equation (5). The distance spectrum, i.e. the amount spectrum of the complex combinatorial values, is shown in the form of a line chart in FIG. 5. Sections 70, 72, 74, 76, which are identified as peak area (=needle) in the future identification, are shown in said FIG. 5.

For identifying "needles", it is now necessary to search the distance spectrum algorithmically for peaks, i.e. for maxima and the associated foot points. Such an algorithm must then identify from the distance spectrum the peaks which belong to the undisturbed Pleth wave and which supply the correct values, consequently. Optionally, the algorithm should additionally permit a certain smoothing of the outputted curves by an elimination of outliers, e.g. by means of a median filter and, possibly by additional temporal averaging. Furthermore, the algorithm should preferably provide a special indication, if the determination of a saturation value is not possible on the basis of the data available.

The distance spectrum must now be examined so as to determine peak areas associated with the so-called "needles", cf. FIG. 4. In the following, a preferred embodiment for identifying peak areas in the distance spectrum will be explained: for the sake of simplicity, these areas will only be referred to as peaks hereinbelow. It is, however, pointed out that the embodiment described is only one preferred embodiment for identifying peaks; alternative methods, which are suitable for identifying peaks and which deviate from the method described, can be used as well.

In the preferred embodiment for indentifying peal areas, the following steps are carried out:

1. search for highest peak that fulfills the maximum criterion, cf. hereinbelow;
2. search foot point on the right that fulfills the foot point criteria, cf. hereinbelow;
3. search foot point on the left;
4. eliminate the found peak between the foot points from the spectrum;
5. repeat steps 1 to 5 until a maximum number of 10 peaks has been found or the residual spectral lines are below a minimum threshold, e.g. 3%; and
6. accept all peaks that fulfil the peak criteria, cf. hereinbelow.

Maximum Criterion

The maximum does not lie at the edge of the spectrum, i.e. for the contact edges, i.e. the foot points, of a cut-out peak 10 Hz are the upper limiting frequency and 0.5 Hz are the lower limiting frequency.

Foot Point Criteria

A foot point must fulfil one of the following criteria:

it must abut on a peak which has already been eliminated, but at least at a distance of one line from said peak;==>new foot point=old peak edge. Hence, a common foot point exists;

the amplitude of two successive lines lies below 25% of the amplitude of the peak==>foot point=first line;

the amplitude of two successive lines lies below 50% of the amplitude of the peak and said lines descend monotonically and gently, i.e. the change in height normalized to the peak height is <5%==>foot point=line in front of the first line.

the amplitude of two successive lines lies below 50% of the amplitude of the peak and the last line rises again==>foot point=line in front of the first line.

Peak Criteria

A peak must additionally fulfil the following criteria:

minimum peak width=three lines (approx. 0.36 Hz); and maximum peak width=4 Hz.

For each peak determined in this way, a plurality of specific characteristics will then be determined, which are used for the future classification of the said peaks:

| time [s] | Needle [#] | fCentr [Hz] | fGgrav [Hz] | relH [%] | absH [norm.] | PSlim [factr] | Asym [factr] | Correl [coeff] | slope [ratio] | SpO2 [%] | Perf [%] | NadelScore |
|---|---|---|---|---|---|---|---|---|---|---|---|---|
| 8.704 | all Time | | | | | | | 0.703 | 0.4 | 104 | | |
| 8.704 | all Freq | | | | | | | 0.851 | 0.41 | 103.3 | | |
| 8.7 | 1 | 1.22 | 1.17 | 100 | 0.05 | 0.37 | −0.07 | 0.982 | 0.45 | 101.8 | 0.06 | 60 |
| 8.7 | 2 | 2.44 | 2.42 | 29 | 0.01 | 0.49 | 0.08 | 0.934 | 0.34 | 106.7 | 0.02 | −4 |
| 8.7 | 3 | 3.54 | 3.59 | 27 | 0.01 | 0.61 | 0.05 | 0.27 | 0.11 | 117.5 | 0.02 | −4 |
| 8.7 | 4 | 8.3 | 8.01 | 15 | 0.01 | 2.08 | −0.01 | 0.422 | 0.41 | 103.6 | 0.01 | −4 |
| 8.7 | 5 | 4.76 | 5.57 | 13 | 0.01 | 2.44 | 0.14 | −0.045 | −0.05 | −1 | 0.01 | −4 |

In the following, the designations used in said table will be explained in detail.

time: signal time since measurement criteria;

needle (peak) [#]: sequence of the peaks/needles found;

allTime: this line does not refer to a peak, but to the whole (preprocessed) time signal in the current FFT window; for the regression analysis the respective temporal samples are taken instead of the frequency lines;

allFreq: this line does not refer to a needle, but to the whole spectrum of 0.5 to 10 Hz; for the regression analysis, all the frequency lines contained therein are used;

fCentr [Hz]: frequency of the longest line of a peak;

fGrav [Hz]: gravity frequency of all lines of a peak;

relH [%]: relative height of the peak in comparison with all peaks found;

absH [norm.]: absolute height of the peak as normalized after the preprocessing; corresponds to the modulation degree or approximately to the perfusion;

Pslim [factr]: slimness factor of the peak, defined as width from foot point to foot point in Hertz;

ASym [facts]: measure for the asymmetry of a peak, defined as $$asy = \frac{(fo - fg) - (fg - fu)}{w},$$

wherein fo=upper foot point, fu=lower foot point, fg=gravity frequency of the pave and w=width of the peak;

Corel [coeff]: correlation coefficient of a needle; i.e. after linear regression analysis of $\hat{S}_R$, $\hat{S}_{IR}$, from the left to the right foot point of a peak; describes the slimness of the needle in the x,y representation (FIG. 4), but not of the peak in the amount spectrum;

slope [ratio]: slope of the regression line; corresponds to the ratio;

SpO2 [%]: SpO2 value determined on the basis of the slope (according to the known empirical relationship, cf. equation 2);

Perf [%]: perfusion index determined on the basis of the height of $\hat{S}_R$, $\hat{S}_{IR}$, at the point fCentr (e.g. by means of the known formula Perf=$0.116 \cdot 2\hat{S}_R + 0.626 \cdot 2\hat{S}_{IR}$);

Nadel Score: number of points according to a classification which will be explained hereinbelow.

The peaks, i.e. needles in the x,y representation, which have been identified and characterized in this way in accordance with the described embodiment of the method according to the present invention, must now be subjected to a selection, since the peaks found will precisely correspond to the fundamental and harmonic waves of the useful signal only if the signal is undisturbed. Normally, it must, however, be assumed that in addition to the useful signal components there are arbitrary disturbance components or that arbitrary disturbance components are superimposed on the useful signal.

On the one hand, disturbance components can spectrally be superimposed on the useful signal peak and can therefore be an integral component of a needle. On the other hand, disturbance components can be present as separately recognizable needles and peaks, respectively. The first-mentioned case is, in principle, uncritical in the case of the method according to the present invention as Ion, as it is assumed that the disturbance within the peak is constant to a certain degree. Such a disturbance only results in a broadening of the needle and in a displacement from the origin. Unless the correlation coefficient is much smaller than 1, this type of background disturbance is substantially eliminated by the method according to the present invention, i.e. the regression analysis.

However, in order to eliminate disturbance peaks which appear separately in the distance spectrum, it will be necessary to subject the peaks, which have been obtained on the basis of the preceding peak identification, to a classification.

In the following, special relevance criteria that can be used for classifying the peaks will be explained in detail. It is, however, apparent that this description only represents a special embodiment; deviating from this embodiment, it is also possible to use only some of the criteria described, to define the limits for these criteria in a different way, and to award points differently.

First of all, the correlation of the time signals (allTime) must be utilizable, e.g. Corel >0.4, since otherwise the (perfectly correlated) useful signal component is not sufficiently large; in this case, the signal should not be further utilized at all for this time.

A peak and the needle associated therewith, which are adapted to be used as useful signal, must have all the following properties:

the peak fits well into a harmonic frequency series comprising one or several other peaks, and the saturation values of the harmonic wave do not differ greatly from one another;

there are as many harmonic waves as possible;

the needle is slim, i.e. its correlation coefficient is close to 1;

the frequency of the fundamental wave is in the physiological or specified range (plus tolerance);

the saturation value lies in a theoretically useful physiological range (plus tolerance);

the perfusion lies in the physiological range; and the pulse rate, i.e. the peak frequency, lies in the physiologically probable range for the patient monitored, e.g. neonate vs. adult.

A peak caused by a disturbance, i.e. a disturber needle, is particularly conspicuous due to the fact that it fails to fulfil one or several ones of the above-demanded properties to a special degree.

The degree of fulfillment of the individual criteria can now be judged in the manner known by a K.O. and a point principle. For this purpose, the following K.O. criteria can, for example, be used, i.e. a peak that does not fulfil these criteria is not taken into account: correlation coefficient >0.5; pulse rate between 30 and 360 bpm; SpO2 between 0% and 110%; and perfusion index between 0.05 (%) and 25 (%).

In addition, points can be awarded for the fulfillment of the following criteria:

+20 points for each suitable harmonic wave, if the frequency deviation of said harmonic wave is less than 10% (or less than 5% for the third and fourth harmonic waves) from the fundamental wave and if the SpO2 deviation thereof is less than 10% from said fundamental wave;

+10 points for a correlation coefficient which is larger than 0.9;

+30 points if the frequency is in the probable pulse frequency range.

The peaks and the associated needles can also be evaluated on the basis of tendency variations with regard to a reference value that was ascertained in a preceding run. In so doing, e.g. +20 points can be awarded to a respective peak for small frequency variations (<10% rel), small perfusion variations (<10% rel) or small saturation variations (<5% abs).

In addition, it is also possible to use K.O. criteria for excessively large tendency variations with regard to a reference value from the preceding algorithm cycle when the score for a peak and the associated needle, respectively, is comparatively low. Hence, peaks will be rejected, which fulfill the criteria following hereinbelow and which have a low point value.

within a short period (15 seconds) after the start of the value output:

frequency variation outside of −20%. rel . . . +30% rel perfusion index variation outside of −20% rel . . . +40% rel saturation variation outside of −10% abs . . . +5% abs;

in the period following said period (>15 seconds):
frequency variation outside of −40% rel . . . +80% rel
perfusion index variation outside of −40% rel . . . +80% rel
saturation variation outside of −15% abs . . . +30% abs;

When a summed needle score has been ascertained in this way for each peak, i.e. for each associated needle, the values of the peak whose score is the highest and amounts to at least 60 points are used for outputting in accordance with the embodiment described. On the basis of the characteristics for this peak, cf. table 1 hereinbefore, the saturation value SpO2 for this peak is then outputted as the saturation value ascertained. In addition, the gravity frequency of this peak can be outputted as the pulse rate ascertained and the perfusion index of this peak can be outputted as the perfusion ascertained.

Optionally, it is then possible to filter individual ones or each of the above-mentioned values ascertained. The value triple can, for example, be inputted together with the last two value triples of the preceding algorithm cycles into a median filter so as to eliminate possible outliers, if an incorrect needle should, by mistake, not have been filtered out by the above identification and classification method. The median triple ascertained by the median filter then provides the reference values which have been described hereinbefore and which can be used for evaluating the tendency. For smoothing strongly dynamic or noisy values, an averaging filter, e.g. a 5 value deep box-car averaging filter, can additionally be connected downstream of said median filter.

If a needle cannot be found by means of the method mentioned hereinbefore, or if none of the needles has a predetermined minimum number of points, the old set of values can be maintained for a predetermined period of time, which may be in a range of from 20 to 40 seconds. Subsequently, a special report, INOP report, is produced, which shows that no utilizable values are produced for the time being. The values can be set to "?" or "0" in this way.

A special case can occur if, in spite of a useful signal, no peaks or needles are found because e.g. a very arhythmic pulse pattern exists. In this case, a special treatment can be carried out. Although it is impossible to calculate a pulse rate due to the arhythmic pulse pattern, an SpO2 value can still be calculated. For use, it is then demanded that the correlation coefficient is better than 0.98 in the time domain (allTime) and in the frequency domain (allFreq) and that the average value of the saturation values from the allTime and frequency correlation does not deviate more than 5% from the reference value. This average value is then outputted as SpO2.

Figure 6:
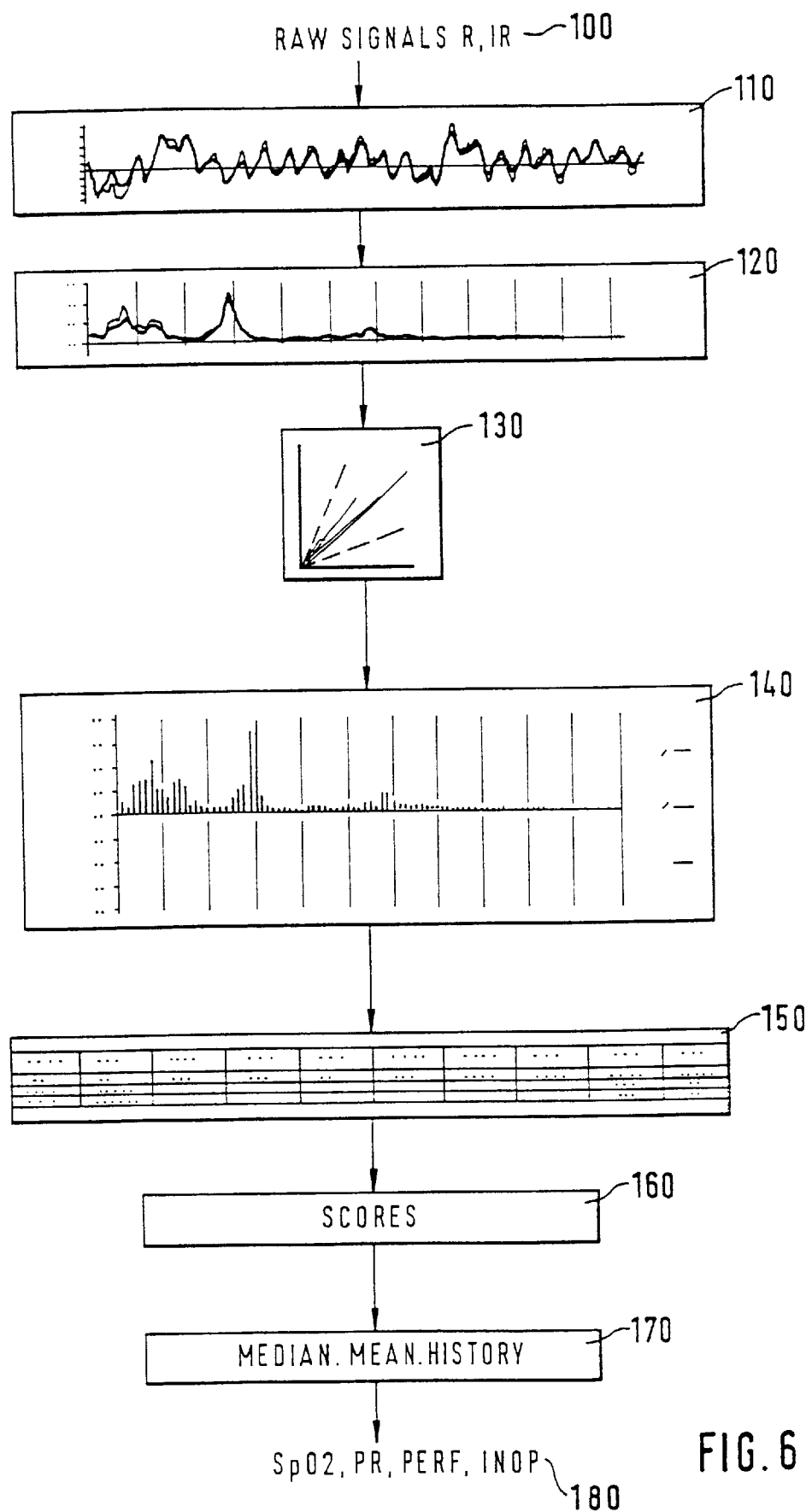
FIG. 6 shows an overview of a preferred embodiment of the method according to the present invention in the form of a flow chart.

FIG. 6 shows an overview of a preferred embodiment of a method according to the present invention in the form of a flow chart. First of all, the raw signals R, IR, which have been obtained from the intensities, are inputted in a processing unit at 100 as has been described hereinbefore. These raw signals R, IR are subjected to preprocessing at 110 so as to perform primarily the so-called baseline correction. Subsequently the values obtained in this way are subjected to an FFT, the resultant amplitude spectra for red and infrared being shown at 120. As shown at 130, these amplitude spectra are converted into an x,y representation; this corresponds to a complex representation of the amplitude spectra. A distance spectrum 140 is obtained from the amount of the complex combinatorial values. From this distance spectrum 140, individual peaks, which fulfil relevant criteria, are selected. Subsequently, these peaks are classified e.g. in the form of a table 150. On the basis of the characteristics of the individual peaks, said peaks have points awarded thereto at 160 so as to identify in this way the peaks that belong to a blood pulse. Following this, a median filtering, an average value formation or a historical evaluation 170 are carried out subsequently. Finally, an SpO2 value, a pulse rate value and/or a perfusion value are outputted as a result of the above selection, or as a result of the amplitude spectra values 120 determined by the above selection, or as a result of the complex combinatorial values 130. If necessary, output of an INOP, instead of an output of the respective values, is effected.

In the following further developments of and alternatives to the above-described special embodiment of the method according to the present invention are described.

It is, for example, possible to determine the above-described peek determination in the red and/or infrared spectrum separately. For this purpose, the ratio following hereinbelow is formed for each sample of the FFT with $a_{IR}$ and $a_R$ as a Fourier coefficient: $ratio(f)=a_R(f)/a_{IR}(f)$. For determining the desired SpO2, the following frequency components are then excluded: all the frequency components for which a Fourier coefficient is smaller than an absolute minimum value so as to avoid quantization problems. Furthermore, all frequency components below a relative detector threshold are excluded. The detector threshold could be defined as a descending curve, e.g. an $1/f$ shape, $1/f^2$ shape, $e^{-x}$ shape, in dependence upon the maximum Fourier coefficient $a_{max}$, e.g. ½ $a_{max}$. Only the frequency values above said threshold are then used for a ratio. Subsequently, a mean ratio is formed by the median, whereupon the standard deviation of all ratios is calculated. Above a specific standard deviation, an INOP is outputted instead of an SpO2 value. Following this, all ratios which differ from the median by a factor of the standard deviation, e.g. one standard deviation, are eliminated. The residual ratio points are used for forming the average value. This results in the SpO2 searched for. The pulse rate would be the frequency at the maximum value $a_{max}$.

What is claimed is:

1. A method of determining at least the concentration of a blood component from the intensity of electromagnetic waves with at least two selected wavelengths which are reflected by a patient's tissue or transmitted through the patient's tissue, said method comprising the following steps:

(a) converting the intensities of received electromagnetic signals into at least one first and one second time-dependent electric signal;

(b) time-discretely transforming the first and the second time-dependent electric signal into the frequency domain for determining first and second spectral values of the first and of the second signals;

(c) selecting physiologically relevant first and second spectral values by evaluating said first and second spectral values according to criteria selected in accordance with the patient's physiological parameters; and (d) calculating the concentration of the blood component making use of the selected first and second spectral values.

2. The method according to claim 1, wherein, in addition to the concentration of the component, at least one of a pulse rate or a perfusion index is calculated making use of the selected first and second spectral values.

3. The method of claim 1, wherein step (c) comprises the steps of:
- (c1) forming complex combinatorial values from said first and second spectral values; and
- (c2) selecting combinatorial values by evaluating the complex combinatorial values according to criteria that are selected to be physiologically relevant to the patient;

and step (d) comprises a step of:
- (d1) calculating a concentration of the component using the selected combinatorial values.

4. The method according to claim 3, wherein, prior to the time-discrete transformation into the frequency domain, said first and second time-dependent signals are subjected to preprocessing for removing time-dependent drift components from said first and second signals.

5. The method according to claim 3, wherein the time-discrete transformation is carried within a selected time window, using a Fourier transformation.

6. The method according to claim 3, wherein the selection of the combinatorial values is carried out on the basis of maximum value ranges in a spectrum of magnitudes of each of the complex combinatorial values.

7. A method according to claim 6, wherein as the given criteria for the physiological relevance of the complex combinatorial values at least two of the following are used: width of the maximum value range; frequency of the maximum value in the maximum value range; gravity frequency of all combinatorial values in the maximum value range; position of the maximum value range with regard to further maximum value ranges in the amount spectrum; saturation value obtained for the maximum value in the maximum value range; perfusion index determined from said maximum value in said maximum value range; pulse rate determined from the gravity frequency in said maximum value range.

8. A method according to claim 7, wherein steps (a), (b), (c1), (c2), and (d1) are cyclically repeated, the given criteria comprising in addition at least one of the following ones: deviation of the frequency of the maximum value of the maximum value range, the perfusion index, or the saturation value from reference values determined in the course of a preceding cycle.

9. A method according to 3, wherein a pulse rate is additionally determined making use of the selected combinatorial values.

10. The method according to claim 3, wherein a perfusion index is additionally determined making use of the selected combinatorial values.

11. A method according to claim 3, wherein steps (a), (b), (c1), (c2), and (d1) are cyclically repeated, the concentration values obtained during several cycles being subjected to filtering or to averaging.

12. The method according to claim 1, wherein the concentration of the component being determined is arterial oxygen saturation.

13. An apparatus for determination of at least the concentration of a blood component from the intensity of electromagnetic waves with at least two selected wavelengths which are reflected by a patient's tissue or transmitted through the patient's tissue, comprising:
- means for converting the intensities of the received electromagnetic signals into at least one first and one second time-dependent electric signal;
- means for time-discretely transforming the first and of the second electric signal into the frequency domain for determining first and second spectral values of the first and of the second time-dependent signals;
- means for selecting physiologically relevant first and second spectral values by evaluating said first and second spectral values according to criteria that are selected to be physiologically relevant to the patient; and
- means for calculating the concentration of the component making use of the selected first and second spectral values.

14. The apparatus of claim 13 wherein the means for selection comprises:
- means for forming complex combinatorial values from said first and second spectral values, and
- means for selecting physiologically relevant combinatorial values by evaluating the complex combinatorial values according to given criteria for the physiological relevance thereof.

* * * * *

UNITED STATES PATENT AND TRADEMARK OFFICE
CERTIFICATE OF CORRECTION

PATENT NO.   : 6,122,535
DATED        : September 19, 2000
INVENTOR(S)  : Kaestle, et. al.

It is certified that error appears in the above-identified patent and that said Letters Patent is hereby corrected as shown below:

In the block providing the inventor information on the patent cover page, please correct to read as follows:

"Inventors: Siegfried Kaestle, Nufringen; Hedwig [Block] <u>Blank</u>; Michael [Block] <u>Blank</u>, both of Boeblingen, all of Germany"

Signed and Sealed this

First Day of May, 2001

Attest:

NICHOLAS P. GODICI

Attesting Officer     Acting Director of the United States Patent and Trademark Office